United States Patent [19]

Belkevich et al.

[11] 4,272,527

[45] Jun. 9, 1981

[54] MEDICINAL PREPARATION CONTAINING THE EXTRACT OF PEAT WAX RESIN

[76] Inventors: Peter I. Belkevich, ulitsa Kulman, 15, kv. 55; Solomon J. Buslovich, ulitsa Volgogradskaya, 27, kv. 49; Elena F. Dolidovich, ulitsa D. Serdicha, 3, kv. 58; Fanya L. Kaganovich, ulitsa Kozlova, 8/1, kv. 88; Oktyabr P. Komov, ulitsa Ya. Kolasa, 27, korpus 2, kv. 30; Ljudmila P. Timofeeva, prospekt Lenina, 40, kv. 34, all of Minsk, U.S.S.R.

[21] Appl. No.: 15,200

[22] Filed: Feb. 26, 1979

[51] Int. Cl.³ .............................................. A61K 35/78
[52] U.S. Cl. ..................................................... 424/195
[58] Field of Search ......................................... 424/195

[56] References Cited

PUBLICATIONS

Chem. Abstracts 88:25414t–citing Bel'kevich et al. and 88:25416v–17W.
Chem. Abstracts 77:52219n.
Chem. Abstracts 78:88526v.

*Primary Examiner*—Douglas W. Robinson
*Attorney, Agent, or Firm*—Lackenbach, Lilling & Siegel

[57] ABSTRACT

A medicinal preparation for treatment of skin diseases consists of an active principle, which is an ethanol extract of peat wax resin, obtained by ethanol extraction of peat wax resin at the ethyl alcohol boiling point, and a pharmaceutical vehicle.

The proposed medicinal preparation has a high therapeutic efficacy, it is well tolerated by patients, and does not produce sensitization. The medicinal preparation is odorless and does not soil linen.

2 Claims, No Drawings

MEDICINAL PREPARATION CONTAINING THE EXTRACT OF PEAT WAX RESIN

FIELD OF THE INVENTION

This invention relates to medicine, and more particularly it relates to a medicinal preparation for treating skin diseases, such as various forms of eczema, neurodermatitis, psoriasis, and trophic ulcer.

The proposed preparation is novel and has not been described in the literature.

SUMMARY OF THE INVENTION

According to the invention, the medicinal preparation comprises an active principle, viz. an ethanol extract of peat wax resin obtained by extraction of peat wax resin with ethyl alcohol at the ethyl alcohol boiling point, and a pharmaceutical ointment vehicle.

The ethanol extract contains natural physiologically active substances such as sterols, and also estrogenic compounds.

DETAILED DESCRIPTION OF THE INVENTION

A medicinal preparation containing from 2 to 10 percent of tar (coal or charcoal tar) as an active principle in combination with a pharmaceutical vehicle for ointment, the latter comprising lanolin, persic oil, and distilled water is known to the art. The ratio of the components in the ointment varies depending on the clinical nature of the disease. Apart from tar, petrolatum, inchthyol and trichloroamine, other substances are also used as the active principle. However, external use of medicinal preparations containing said substances often provokes inflammation of the treated skin, folliculitis, and photosensitization. Medicinal preparations containing corticosteroids are also often used to treat said skin diseases. But prolonged use of these preparations produces an unfavourable effect on the adrenal function in the patients.

As compared with the known preparations, the proposed medicinal preparation has a more pronounced therapeutic efficacy and is better tolerated by patients. It does not produce irritation and is non-toxic. Nor does it produce sensitization in the patients. The medicinal preparation does not soil linen or bandaging material.

The medicinal preparation was tested pharmacologically for harmlessness on 110 albino mice, 154 albino rats, 6 rabbits, and 6 dogs.

The preparation was given intraventricularly, using a probe needle, to 21 rats and 40 albino mice. The single dose of the preparation did not exceed 1 ml for albino mice and 3 ml for albino rats. Sunflower seed oil or persic oil was given in the same doses to control animals. The animals were observed for ten days, within which the preparation was given three times a day.

The administration of 10,000 mg/kg and 15,000 mg/kg of the preparation into the stomach of albino rats did not produce toxic action. The animals survived.

The examination of blood taken from the rats to whom the preparation was given into the stomach in a dose of 5,000 mg/kg did not show any pathological shifts (See Table 1).

TABLE 1

Effect of the Medicinal Preparation Introduced into the Stomach of Albino Rats on the Morphology of the Blood (Dose 5 g/kg, n = 7)

| Blood indices | | Before experiment | | Two days following the administration | |
|---|---|---|---|---|---|
| 1 | | 2 | 3 | 4 | 5 |
| Hemoglobin, mg % | | 14.11–12.53 | 13.32 | 15.88–11.42 | 13.65 |
| Erythrocytes, thous | | 7423–6040.6 | 6732 | 8723 | |
| Leucocytes, thous | | 13.203–7.637 | 10.42 | 17.446–8.23 | 12.838 |
| Leukocytal formula, % | Stab neutrophils | 3 | | — | |
| | segmento-nuclear | 20.6 | | 27.5 | |
| | lymphocytes | 72.8 | | 64 | |
| | monocytes | 4.4 | | 5 | |
| | eosinophils | 1 | | 4.4 | |

There were no pathological shifts ten days following the administration of the preparation either.

Traces of proteins, epithelial cells (0-1-2 in the field of vision) and single leukocytes were found in the urine of the animals before the experiment.

The medicinal preparation was given intraperitoneally (into the lower right-hand part of the abdomen) to 21 albino rats. The ointment vehicle was given to controls. Doses of 3,000 mg/kg, 5,000 mg/kg and 6,000 mg/kg, given intraperitoneally, produced clinical manifestations of poisoning. The animals became flaccid, developed adynamia and lost appetite. Some rats perished on the 2–5th day following the administration of the preparation. Three out of the seven animals to whom the preparation had been given in the dose of 3,000 mg/kg, and four of the seven to whom it had been given in the dose of 5,000 and 6,000 mg/kg, perished. Larger doses of the preparation were not given to the animals since otherwise the ointment should have been given in the volume exceeding the allowed maximum.

The analysis of the blood of these animals, made on the 2nd and 5th day after the administration of the preparation, showed that the animals developed neutrophilia (Table 2).

TABLE 2

Effect of the Preparation (Given Intraperitoneally) on the Morphological Composition of the Blood of Albino Rats (n = 7)

| Blood indices | | Before administration | in 2 days | in 4 days |
|---|---|---|---|---|
| Hemoglobin, mg % | | 13.04 | 14.5 | 12.4 |
| | | 13.65–12.43 | 15.55–13.45 | |
| Erythrocytes, thous. | | 5834 | | |
| | | 6485.5–5182.1 | 6930 | 6420 |
| Leukocytes, thous | | 6.275 | 13.450 | 6.850 |
| | | 8.695–3.855 | 18.675–8.225 | |
| Leukocytal formular, % | segmental-nuclear | 29.6 | 80 | 70 |
| | lymphocytes | 64 | 12.5 | 24 |
| | monocytes | 4.2 | 4 | 3 |
| | stab neutrophils | 3 | 3.7 | 2 |
| | eosinophils | 1 | — | 2.3 |
| | Plasma cells | 2 | | |

The administration of 5000 mg/kg and 7500 mg/kg of the preparation into the stomach of albino mice did not produce clinical manifestations of intoxication, and the animals survided. The intraperitoneal administration of 500 mg/kg and 1000 mg/kg of the preparation did not give clinical signs of the intoxication either, and the animals survived.

The ointment was applied onto the skin of albino rats for three weeks. There were no signs of irritation on the skin and the animals survived.

Repeated analyses of blood samples taken from these animals did not show any deviations from normal (Table 3). The analyses of urine showed the presence of large quantities of bacteria and phosphates.

TABLE 3

Effect of Prolonged Epicutaneous Application of the Preparation On the Morphological Composition of Blood of Albino Rats (n = 7)

| Blood indices | in one week | in two weeks |
| --- | --- | --- |
| Hemoglobin, mg % | 13.4 | 12.37 |
|  | 14.74–12.06 | 14.58–10.16 |
| Erythrocytes, thous | 6277.5 | 6831.4 | ish, but the relative masses of the other internal organs did not change compared with those in control animals.

The morphological composition of blood in the experimental animals did not differ from that in controls (See Tables 4 and 5).

The protein content of blood, the sugar content, the activity of the aldolase enzymes, of phosphohexoisomerase in the experimentals animals did not differ from those in controls.

Prolonged application of the medicinal preparation onto dehaired skin sites of six rabbits and 6 dogs did not produce appreciable changes. The skin remained intact and there were no signs of irritation. The animals remained active and mobile, and took food willingly in the entire course of the experiment. No pathological changes in the morphological composition of the blood were found (Table 6, 7).

TABLE 4

Effect of Three-month Epicutaneous Application of the Medicinal Preparation on the Morphological Composition of Blood of Albino Rats

| Blood indices | | Before administration | in 1 month | in 2 months | in 3 months |
| --- | --- | --- | --- | --- | --- |
| Hemoglobin, mg % | | 14.56 | 13.79 | 12.87 | 12.88 |
| | | 14.99–14.13 | 14.22–13.36 | 13.59–12.15 | 13.38–12.38 |
| Erythrocytes, thous | | 6803.6 | 5972.3 | 5685 | 73 61.7 |
| | | 7308700–6298500 | 6241300–5945400 | 5954.6–6.5416 | 7710–3013.4 |
| Leukocytes, thous | | 9731 | 10.369 | 8.833 | 10.271 |
| | | 11.277–8.185 | 12.457–8.281 | 11.830–5.836 | 14.711–5.831 |
| Leukocytal formula, % | stab neutrophils | 1.16 | 1.3 | 1.0 | 1.3 |
| | segmental-nuclear | 30.1 | 47.7 | 44.8 | 29.08 |
| | eosinphils | 1.9 | 1.5 | 1.7 | 1.88 |
| | monocytes | 3.3 | 3.5 | 2.5 | 4.17 |
| | lymphocytes | 64.7 | 46.5 | 51.1 | 64.83 |
| | ESR, mm/hr | | | | 2.5 |

TABLE 5

Effect of Three-month Epicutaneous Application of Sunflower Seed Oil and Lanolin on the Morphological Composition of Blood of Albino Rats (Controls)

| Blood Indices | | Before experiment | in 1 month | in 2 months | in 3 months |
| --- | --- | --- | --- | --- | --- |
| Hemoglobin, mg % | | 13.99 | 14.43 | 13.07 | 12.08 |
| | | 14.2–13.78 | 14.86–14.0 | 14.96–11.19 | 13.17–12.43 |
| Erythrocytes, thous | | 5742.5 | 6817.3 | 6288.3 | 7448.6 |
| | | 6626.1–5458.9 | 7186.6–6448 | 6861.2–5715.4 | 7957.1–6940.1 |
| Leukocytes, thous | | 8.627 | 12.073 | 11.75 | 9.435 |
| | | 10.249–7.005 | 15.598–8.548 | 19.671–3.829 | 11.098–7.722 |
| Leukocytal formula, % | stab neutrophils | 1.7 | 1.1 | 1.7 | 1.6 |
| | segmental-nuclear | 24.9 | 27.9 | 33.6 | 36.21 |
| | eosinophils | 1.0 | 1.5 | 2.4 | 1.6 |
| | monocytes | 5.3 | 2.6 | 3.7 | 4.2 |
| | lymphocytes | 69.2 | 73.9 | 60 | 58.3 |
| | ESR, mm/hr | | | | 3.33 |

| | | 6775200–5779800 | 7796–5866.8 |
| --- | --- | --- | --- |
| Leukocytes, thous | | 9.925 | 6.664 |
| | | 11.938–7.912 | 8.404–4.924 |
| Leukocytal formular, % | stab neutrophils | 1.9 | 1.9 |
| | segmental-nuclear | 44 | 29.4 |
| | eosinophils | 1.5 | 1 |
| | monocytes | 3.7 | 4.3 |
| | lymphocytes | 50.3 | 64.3 |

The experimental animals were treated with the proposed preparation for three months. The observation did not reveal any signs of intoxication in the animals, their skin was not irritated. The rats remained active and took food willingly during the entire experiment.

The gain in weight of the experimental animals did not substantially differ from that in controls. The relative mass of the heart was statistically proved to diminish, Materials for histological studies was taken immediately after the animals were killed. The following methods were used: staining with hematoxylineosin and staining for fat with Sudan III and IV with subsequent staining with hematoxylin. The heart, liver, kidneys, and spleen were also studied. There were no pathological changes in the organs disclosed on section.

The microscopic study of specimens revealed that the daily application of the medicinal preparation on the skin for three months did not produce any specific changes in the internal organs. In some cases the tissues of the organs (liver, kidneys) were infiltrated with lymphoid cells, which, according to the experimental data, cannot be considered as the sign of toxic inflammation, but rather indicates the intensification of the metabolic phenomena or is the morphological manifestation of the changed reactivity.

TABLE 6

Effect of Prolonged Epicutaneous Application of the Medicinal Preparation on the Morphological Composition of Blood of Rabbits

| Blood indices | | Before experiment | In 19 days |
|---|---|---|---|
| Hemoglobin, mg % | | 12.73 | 12.32 |
| | | 13.45–12.01 | 13.1–11.54 |
| Erythrocytes, thous | | 4675,000 | 4648,300 |
| | | 5078,500–4271,500 | 5059,200–4237,400 |
| Leukocytes, thous | | 7.892 | 7.717 |
| | | 9.825–5,959 | 10.585–4.849 |
| ESR, mm/h | | 3.5 | 7 |
| | | 3.64–3.36 | |
| Leukocytal formula, % | stab neutrophils | 1.6 | 2 |
| | segmental-nuclear | 17.3 | 51.8 |
| | lymphocytes | 78.3 | 45 |
| | monocytes | 2.69 | 1.7 |
| | eosinophils | | 1.5 |

TABLE 7

Effect of Prolonged Application of the Medicinal Preparation on the Morphological Composition of Blood of Dogs

| Blood Index | | Initial, m ± | in 21 days |
|---|---|---|---|
| Hemoglobin, mg % | | 14.27 ± 2.4 | 13.14–3.1 |
| Erythrocytes, thous | | 7973 ± 2174 | 8117 ± 2235 |
| Leukocytes, thous | | 15.167 ± 3.1 | 13.2 ± 4.2 |
| ESR, mm/hr | | 3 ± 1 | 4 ± 1.7 |
| Leukocytal formula, in % | | | |
| Leukocytal formular, % | stab neutrophils | 1 | 2 |
| | segmental-nuclear | 76.7 | 72.4 |
| | eosinophils | 3 | 2 |
| | monocytes | 3.67 | 4.5 |
| | lymphocytes | 15.7 | 19.1 |

The allergic action of the proposed medicinal preparation through its contact with skin was studied by daily (within 20 days, except Sundays) epicutaneous application of the preparation onto a dehaired site of the animal back (2×2 cm) in the sensitizing concentration. The preparation was applied in a uniform layer over the whole dehaired site using a glass spatula (used to apply eye ointments). The effect of the preparation was tested after the first ten applications. The allergic action of the preparation was tested epicutaneously. The second test was done in 20 days.

The tests were carried out on 20 guinea pigs (ten experimental animals and ten controls). The ointment vehicle alone was applied onto dehaired skin of controls. During the entire test there were no edemas, reddening, or other visible changes on the skin. The animals remained active, alive, and took food willingly. Neither the first nor the second test revealed any allergic manifestations on the skin of the guinea pig backs.

Since it is impossible to simulate psoriasis or eczema in laboratory animals, we tried the preparation clinically on 150 patients. The group contained 76 men and 74 women, aging from 6 to 65 years. They had the disease from two months to one year (25 patients), from one year to three years (29 patients), from three to five years (31 patients), from five to ten years (33 patients) and over ten years (32 patients).

Of the 150 patients, 82 had psoriasis (the stationary stage in 77 patients, progressing in 5, this number including one patient with arthropathic form of the disease), 49 patients had eczema (exacerbated chronic disease in 20, seborrheal in 3, mycotic in 11, and occupational in 15 patients), three patients had trophic ulcer of the leg, four disseminated neurodermatitis, ten had dermatitis and two lichen ruber planus. The proposed medicinal preparation was applied onto the affected skin in a thin layer, two times a day. Wherever possible the affected sites, were then bandaged with parchment paper and gauze. The preparation was applied every day until stable improvement was attained, but the course would not continue longer than 3–4 weeks. Some patients were given repeated courses after an interval of one or two weeks. The quantity of the preparation used and the areas treated with it were not limited. About 200–300 g of the preparation were spent to treat one patient for 3–4 weeks.

During the course of treatment with the preparation the subjective sensations (burning, itching) diminished in the patients within one or two days, and the objective improvement was attained by the 4th or 5th day: hyperemia and infiltration subsided, erosions were healed, and scales fell off.

The results of the clinical studies of the medicinal preparation were as follows: 28 patients were cured clinically, 40 patients improved considerably, 59 patients improved, and in 22 patients the medicinal preparation failed to produce any effect.

The preparation was well tolerated by the patients, but in two of them (at various terms after the treatment) itching was intensified insignificantly, they felt burning at the sites of application of the ointment, and new eruptions appeared. In these cases the therapy was suspended for two weeks, and sometimes the preparation was no longer used at all.

Contraindications: the preparation should not be used in exudative forms of eczema.

The preparation is dispensed in the form of an ointment having the following composition: from 1 to 10 percent by weight of ethanol extract of peat wax resin, 50.0 percent by weight of lanolin or petrolatum (softer excipients can also be used), from 15 to 38 percent by weight of sunflower seed oil, persic oil, or olive oil, and 10 percent by weight of distilled water. The preparation should be stored at a temperature of 0.5° C. in dark bottles. If the components separate on standing, the preparation should be stirred before use.

The preparation can be kept for five years.

It is recommended that the active principle should be contained in the preparation in the quantity from 1 to 10 percent by weight.

The recommended vehicle for the ointment is lanolin with persic oil, petrolatum with sunflower seed oil, or with olive oil.

The ethanol extract of peat wax resin is prepared as follows.

Peat wax resin is loaded into an extraction vessel provided with a reflux condenser and a stirrer, and a five-fold quantity of ethyl alcohol is then added. The mixture is stirred for one hour at a temperature at which ethyl alcohol boils. Live steam is used to heat the extractor. The supernatant of the resultant two-phase mixture is the ethanol extract of peat wax resin. The extract is transferred into an evaporation tank, and a new portion of ethyl alcohol is added into the extractor. The extraction is repeated two times. The extracts are then collected and the solvent removed by distillation.

What is claimed is:

1. A method for the treatment of skin diseases selected from the group consisting of eczema and psoriasis, comprising the topical administration of a medicinal preparation containing a therapeutically effective amount of an ethanol extract of peat wax resin in conjunction with a pharmaceutically acceptable ointment vehicle.

2. The method according to claim 1, wherein the active principle varies in an amount of from 1 to 10 percent by weight of the medicinal preparation.

* * * * *